(12) United States Patent
Pacey et al.

(10) Patent No.: US 8,986,204 B2
(45) Date of Patent: Mar. 24, 2015

(54) TELEMEDICINE SYSTEMS AND METHODS

(76) Inventors: John Allen Pacey, Vancouver (CA);
Reza Ahmadian Yazdi, Richmond (CA);
Shahrad Payandeh, Port Coquitlam
(CA); Siamik Hafizi Moori, Burnaby
(CA)

( * ) Notice: Subject to any disclaimer, the term of this patent is extended or adjusted under 35 U.S.C. 154(b) by 517 days.

(21) Appl. No.: 12/947,745

(22) Filed: Nov. 16, 2010

(65) Prior Publication Data

US 2011/0178373 A1 Jul. 21, 2011

Related U.S. Application Data (60) Provisional application No. 61/261,739, filed on Nov. 16, 2009, provisional application No. 61/350,849, filed on Jun. 2, 2010.

(51) Int. Cl.
| | |
|---|---|
| *A61B 5/00* | (2006.01) |
| *A61B 1/267* | (2006.01) |
| *A61B 5/04* | (2006.01) |
| *A61B 5/02* | (2006.01) |
| *G06F 19/00* | (2011.01) |
| *A61B 1/00* | (2006.01) |

(52) U.S. Cl.
CPC .............. *A61B 1/267* (2013.01); *A61B 5/0002* (2013.01); *A61B 5/04* (2013.01); *A61B 5/02* (2013.01); *G06F 19/3406* (2013.01); *G06F 19/3425* (2013.01); *G06F 19/3418* (2013.01); *A61B 2505/01* (2013.01); *Y10S 128/92* (2013.01)
USPC ........... 600/300; 600/301; 600/509; 600/185; 705/3; 709/201; 709/217; 128/920; 340/539.12

(58) Field of Classification Search
None
See application file for complete search history.

(56) References Cited

U.S. PATENT DOCUMENTS

| | | | | |
|---|---|---|---|---|
| 5,469,541 | A * | 11/1995 | Kingman et al. .............. | 345/545 |
| 5,701,904 | A * | 12/1997 | Simmons et al. ............. | 600/301 |
| 6,112,224 | A * | 8/2000 | Peifer et al. .................... | 709/202 |
| 6,123,666 | A * | 9/2000 | Wrenn et al. ................. | 600/188 |
| 6,381,484 | B1 * | 4/2002 | Ayanruoh ...................... | 600/407 |
| 6,535,714 | B2 * | 3/2003 | Melker et al. ................. | 434/350 |
| 8,038,593 | B2 * | 10/2011 | Friedman et al. .............. | 600/26 |
| 2004/0215490 | A1 * | 10/2004 | Duchon et al. ..................... | 705/2 |
| 2007/0118389 | A1 * | 5/2007 | Shipon .............................. | 705/1 |
| 2009/0036790 | A1 * | 2/2009 | Landesberg et al. .......... | 600/529 |
| 2009/0307328 | A1 * | 12/2009 | Nuttall et al. ................. | 709/212 |
| 2010/0049009 | A1 * | 2/2010 | Muirhead ...................... | 600/301 |
| 2010/0256482 | A1 * | 10/2010 | Peters et al. .................. | 600/424 |
| 2011/0106557 | A1 * | 5/2011 | Gazula .............................. | 705/3 |
| 2011/0166465 | A1 * | 7/2011 | Clements et al. ............. | 600/509 |
| 2011/0190595 | A1 * | 8/2011 | Bennett et al. ................ | 600/301 |

* cited by examiner

*Primary Examiner* — William Thomson
*Assistant Examiner* — Marie Archer
(74) *Attorney, Agent, or Firm* — Foster Pepper PLLC; Richard A. Koske; P. G. Scott Born (57) ABSTRACT

Methods and systems for telemedicine are provided. A method for operating a telemedicine base unit includes initiating a remote connection with a remote care site. The remote care site may be selected from a plurality of remote care sites based on an attached medical device. The telemedicine base unit transmits the output from the attached medical device to the remote care site. Medical device operating instructions and other information are received from the remote care site. The medical device operation instructions provide guidance for operating the attached medical device.

15 Claims, 10 Drawing Sheets

TELEMEDICINE SYSTEMS AND METHODS

RELATED APPLICATIONS

This application claims priority to and the benefit of the filing date of U.S. Provisional Patent Application No. 61/261,739 filed Nov. 16, 2009 and U.S. Provisional Application Ser. No. 61/350,849 filed Jun. 2, 2010, both of which are hereby incorporated by reference in their entirety.

This application describes embodiments that can be usefully combined with, or used in conjunction with applicant's other inventions described in the following patents and co-pending applications, each and all of which are incorporated by reference in their entirety: U.S. Pat. No. 6,142,144 filed as U.S. patent application Ser. No. 09/060,891 on Apr. 15, 1998; U.S. Pat. No. 6,655,377 filed as U.S. patent application Ser. No. 10/356,705 on Jan. 30, 2003; U.S. patent application Ser. No. 11/285,743 filed Nov. 21, 2005; U.S. Provisional Patent Application No. 60/862,192 filed Oct. 19, 2006; U.S. patent application Ser. No. 11/645,086 filed Dec. 21, 2006; U.S. patent application Ser. No. 11/925,868 filed Oct. 27, 2007; U.S. Provisional Patent Application No. 61/027,377 filed Feb. 8, 2008; U.S. patent application Ser. No. 12/368,298 filed Feb. 9, 2009; U.S. Provisional Patent Application No. 61/029,268 filed Feb. 15, 2008, and U.S. Provisional Patent Application No. 61/319,835 filed Mar. 31, 2010.

TECHNICAL FIELD

The present disclosure relates to methods, techniques, and systems for telemedicine and, in particular, to methods, techniques, and systems for using telemedicine to enable remote care.

BACKGROUND OF THE INVENTION

Endotracheal intubation provides the current preferred method for control of an airway for mechanical ventilation. The process involves passing an endotracheal tube (ETT) through the mouth, past the tongue, and to and through the vocal cords and larynx to access ("access" might be a broader and more accurate term—a cuff seals, but cuffs not always used) the airway. This protects the patency of the airway and protects the airway from aspiration of gastric contents, foreign substances, or secretions. The complex and invasive procedure occurs regularly in surgery and in emergency departments throughout the word, including large hospitals in metropolitan areas with large experienced staffs and remote hospitals and clinics in rural areas with less experienced medical personnel. In addition, intubation is increasingly performed in pre-hospital settings such as ambulances, medical evacuation helicopters, and by military medics in combat and near-combat situations. It is well known that failure to intubate, when required, can lead to death or serious injury. Intubation is a complex process which presents numerous challenges, as well as a myriad of possible injuries to the patient short of death from de-oxygenation. There are numerous factors that make airway management so difficult, such as limited training, poor equipment, environmental factors (cold, snow, sand, rain, sun, and/or terrain), patient location, anatomy, blood, vomitus, secretions and other factors. Nonetheless, even when using a laryngoscope for the first time untrained professionals can successfully intubate, if they are "walked" through the process.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

In the following description, certain specific details are set forth in order to provide a thorough understanding of various embodiments of the invention. However, one skilled in the art will understand that the invention may be practiced without these details or with various combinations of these details. In other instances, well-known systems and methods associated with, but not necessarily limited to, telemedicine, laryngoscopes, video laryngoscopes, heart monitors and methods for operating the same may not be shown or described in detail to avoid unnecessarily obscuring descriptions of the embodiments of the invention.

Embodiments described herein provide enhanced methods, systems and techniques for providing real time instruction, oversight and collaboration during medical procedures. Example embodiments provide a telemedicine base unit, with an installed telemedicine facilitation system, which enables a user to connect a medical device to the telemedicine base unit. Example medical devices may include 18-80 lead ECG tracks, 12 lead ECG, Temperature Monitoring Devices, Laryngoscopes, Cardiac Monitors, respiratory, pulse oxymetry, microscopes, ultrasound devices, and/or any sensors designed to acquire medical patient info. The telemedicine base unit is preferably capable of connecting with a doctor, hospital or other care provider for instruction on how to operate the connected medical device. The base unit may also connect with consultants or other informed parties. The telemedicine base unit enables multi-directional communication of audio, video, data and other graphical symbols between a remote care site and the user of the base unit. The telemedicine base unit enables successful and supervised care of a patient. This may even occur in a pre-hospital setting such as in a first responder or field military environment.

For example, in one embodiment of the disclosed invention, an example video laryngoscope is provided with an example telemedicine base unit. The example video laryngoscope is connected to the example telemedicine unit and the example telemedicine unit displays the view from the camera mounted on the example video laryngoscope. The example telemedicine unit then preferably remotely connects and communicates with a remote care site that specializes in intubation procedures (or has personnel who are experts in such procedures). The example telemedicine base unit transmits video and audio information to the remote care site and receives through a wired or wireless connection video and/or audio connection operating instructions that enables a user to operate the example video laryngoscope to perform an intubation procedure.

An embodiment of the current invention advantageously provides the ability to intubate in, for example, a pre-hospital situation, with an on call doctor or care giver guiding the intubator through the procedure. The on call doctor or care giver is further advantageously able to see the view from a camera on the laryngoscope, a view from the camera on the base unit and the ability to hear the intubator. In other embodiments other alternate medical devices may be connected to the example telemedicine base unit and provide different information to the on call doctor, such as cardiac information in the case of electrocardiographs.

A telemedicine base unit may be a device (e.g., computer, portable computer, mobile computing device, and/or any device capable of wired or wireless connection to a network), from which it establishes multidirectional communications (e.g., audio, video, graphics and/or any other indication of content) viewable in the form of medical instructions for operating a medical device and/or performing a medical procedure. The telemedicine base unit communicates with remote medical sites through GSM, GPRS, CDMA, EV-DO, EDGE, DECT, IS-136/TDMA, iDEN, satellite bands, LAN, Military Networks, 3G, 4G and Wi-Fi Networks or any other audio/video link. The telemedicine base unit may communicate directly with a remote care site, or may communicate with a server configured to relay a communication to a remote care site.

Figure 1:
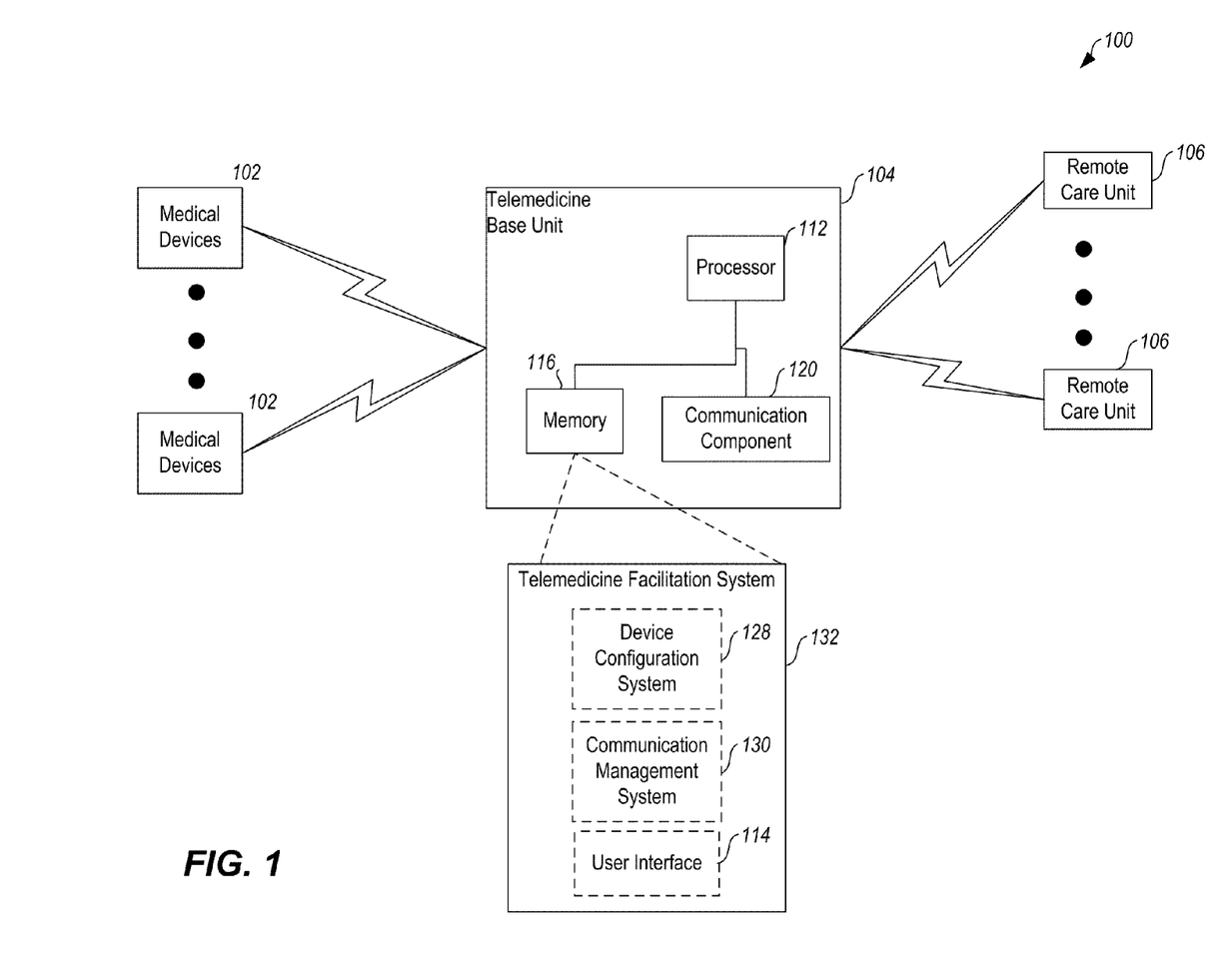
FIG. 1 is an example block diagram of an example telemedicine environment.

FIG. 1 is an example block diagram of an example telemedicine environment 100 that includes a Telemedicine Base Unit ("TBU" or "TB Unit") 104, a Telemedicine Facilitation System ("TFS") 132 (e.g., a code module/component), one or more medical devices 102 that provide a medical output (e.g. video feeds, vital signs, EKG signals, and/or other physiological outputs from a patient), one or more remote care units 106 (e.g. computers, video conferencing devices, portable devices and/or any device capable of transmitting and receiving audio/video either directly or indirectly to the telemedicine base unit). The TBU 104 includes a processor 112, local memory 116, and a communication component 120. The components of the illustrated TFS 132 provide various logic (e.g. code, instructions, etc.) and/or services related to the operation of the TBU 104, and provide the instructions that when executed receive output data from the medical devices 102 and manage a multidirectional communication with the remote care units 106. The TFS 132 may provide other capabilities such as providing stored video or audio, providing instructional functions, connecting with other patient monitoring devices either wired or wirelessly and or other administrative tasks related to the implementation of the telemedicine environment 100.

The TFS 132 comprises a device configuration system 128 a communication management system 130 and a user interface 114. The device configuration system 128 is configured to determine the identity of an attached medical device 102 and to configure the TBU 104 to receive output signals from the identified attached medical device 102. The communication management system 130 is configured to transmit (e.g. forward, send, communicate, etc.) the output signals from the attached medical devices 102 and various inputs related to the TBU 104 to the remote medical sites 106 and to receive medical instructions on how to operate the attached medical device from the remote medical sites 106. A communication, in some embodiments, may include audio/video/graphical indications from the TBU 104 to the remote medical sites 106, and may include the receipt of audio/video/graphical indications from the remote medical sites 106. The communications from the remote medical sites 106 may, for example, include step by step instructions for operating the attached medical device 102. The TFS 132 includes a user interface 114 to display medical device information, patient status information, and/or received instructions from the remote medical sites 106.

Figure 2:
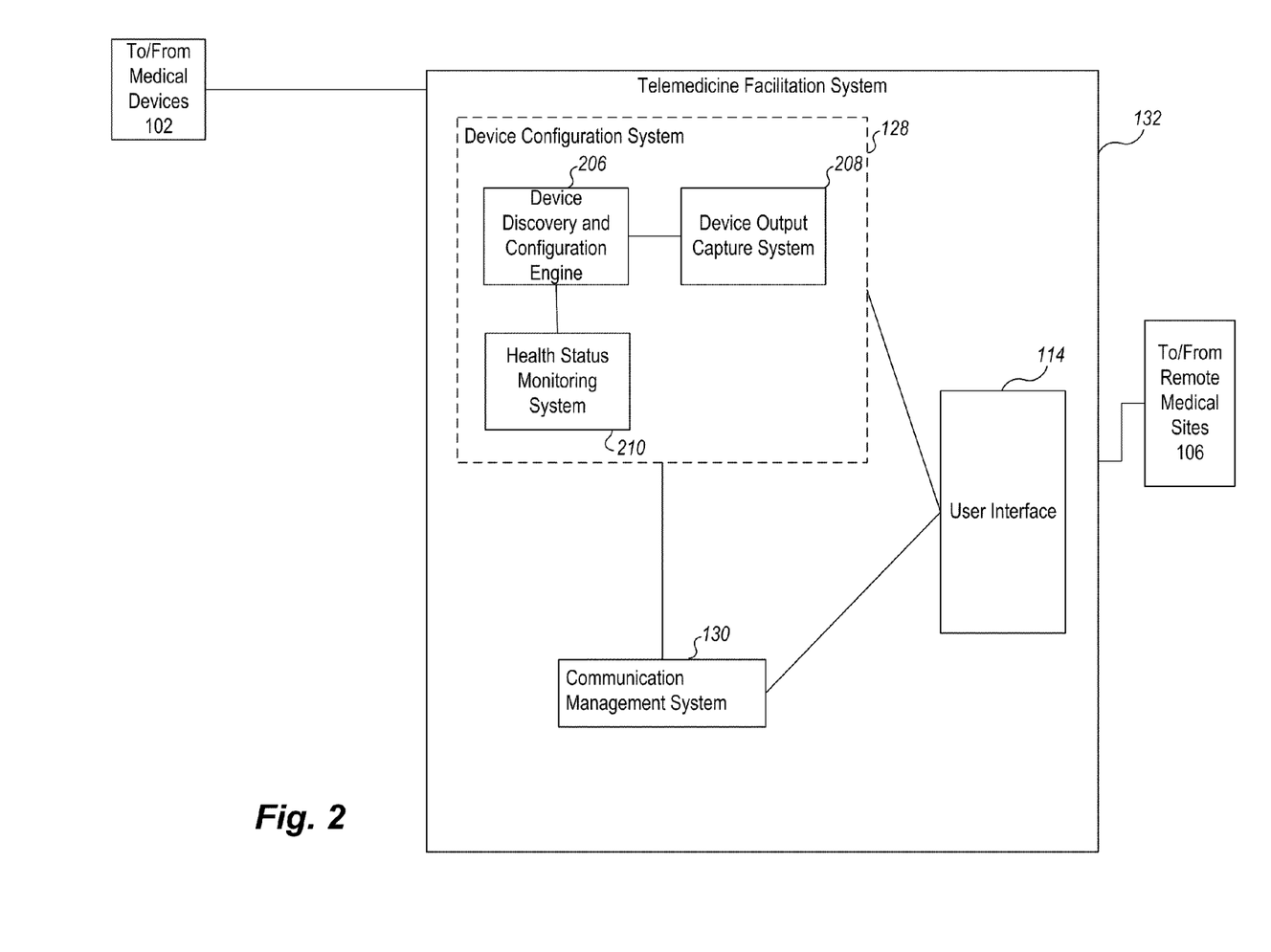
FIG. 2 is an example block diagram of example components of an example telemedicine facilitation system.
Figure 3A:
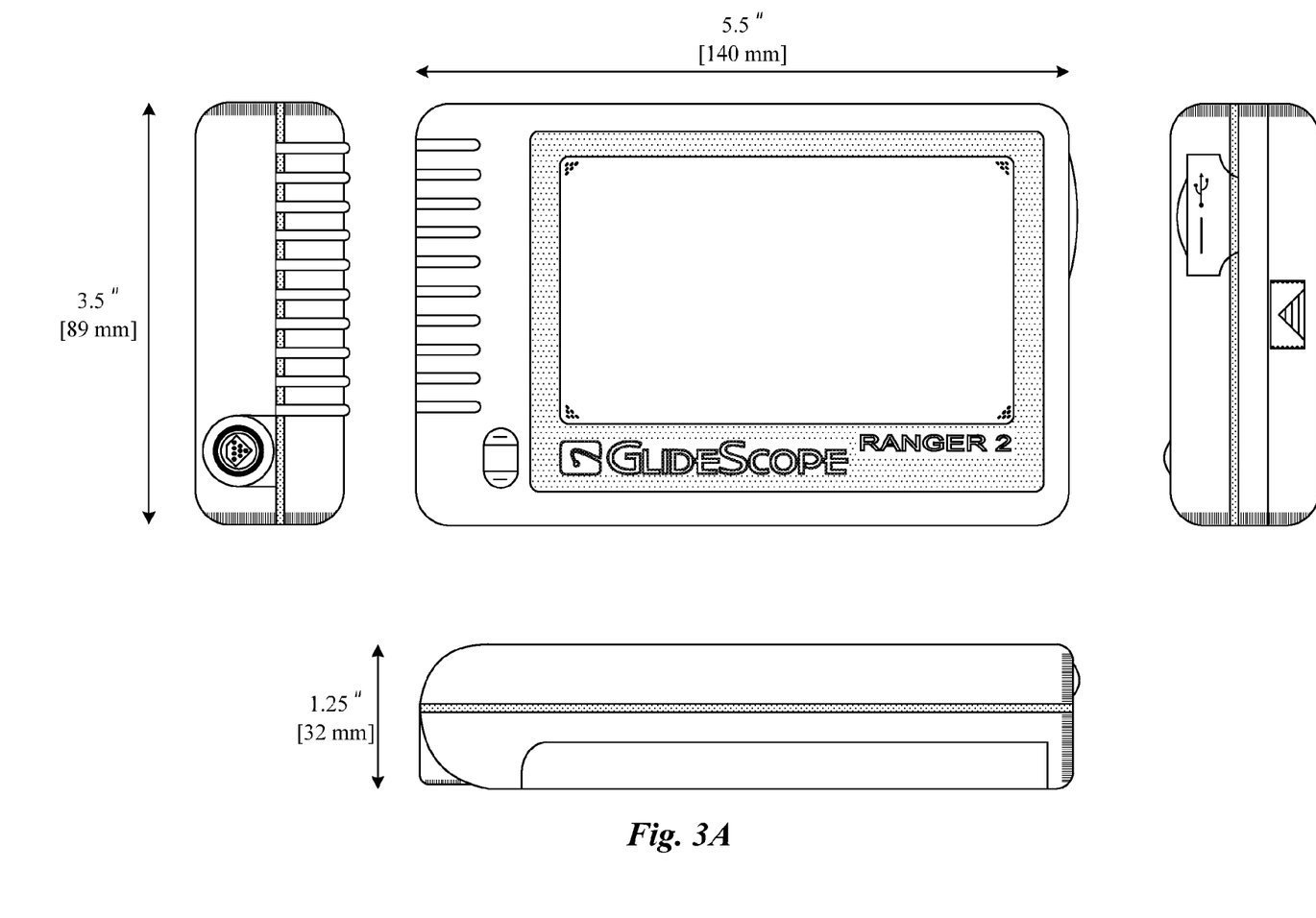
FIGS. 3A-3D show multiple views of example Telemedicine Base Units according embodiments of the current invention.
Figure 3B:
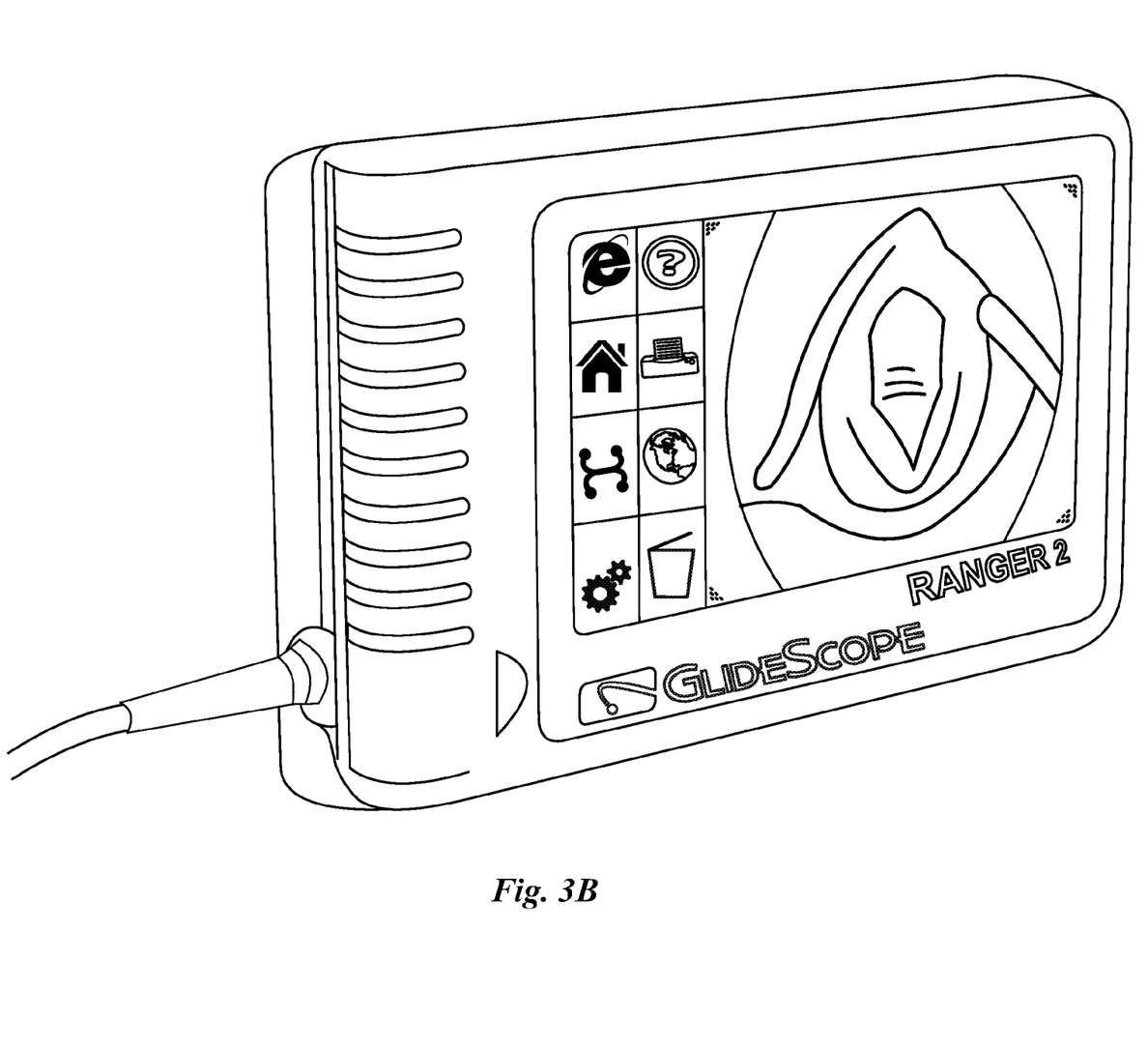
Figure 3C:
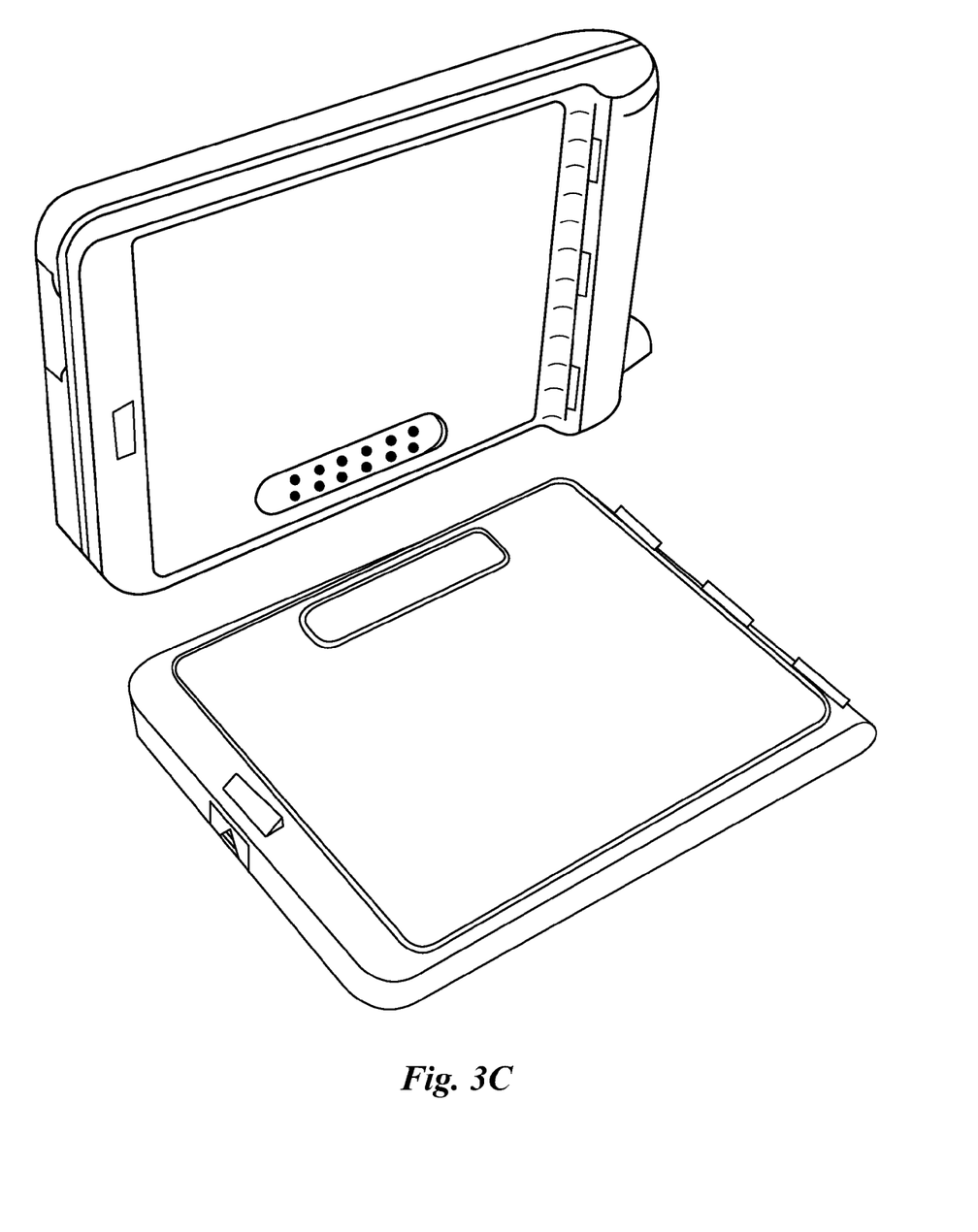
Figure 3D:
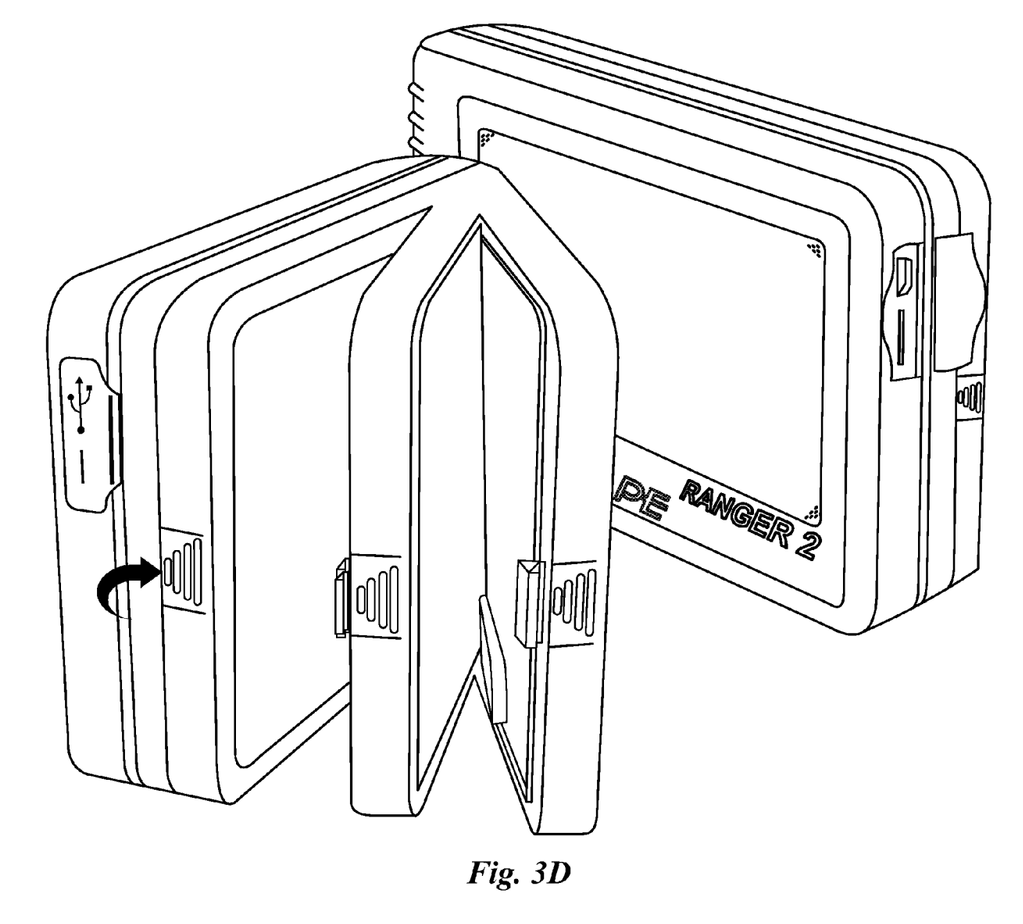

FIG. 2 is an example block diagram of example components of an example telemedicine facilitation system 132. In one embodiment, the telemedicine facilitation system 132 comprises one or more functional components/modules that work together to enable multidirectional communications with remote medical sites 106 and to receive an output from the medical devices 102. The components may be implemented in software or hardware or a combination of both. The TFS 132 includes a device configuration system 128, a communication management system 130 and a user interface 114. The device configuration system 128 includes a device discovery and configuration engine 206, a device output capture system 208 and a health status monitoring system 210. The device discovery and configuration engine 206 receives an indication of an attached device and based on the attached device, the device discovery and configuration engine 206 configures the telemedicine base unit to operate and/or to receive output signals from the attached medical device. The device output capture system 208 is configured to receive an output from the attached device and to store the output in the telemedicine base unit memory or to provide the output to a communication management system 130 for transmission to a remote medical site 106. The health status monitoring system 210 is configured to initiate a connection with one or more patient monitoring devices, either through a wired or wireless connection. For example the health status monitoring system may link, using a Bluetooth connection, with a system monitoring a patient's body temperature, pulse rate, cardiac output, for respiratory, pulse oxymetry, microscopes, ultrasound, blood pressure, blood sugar, and/or respiratory rate.

The communication management system 130 is configured to receive an indication of an attached device and then is further configured to initiate a communication with a remote care site. The remote care site is preferably able to provide medical instructions to a user that enables the user to operate the attached device. For example, a device for monitoring the heart may result in a communication with a heart center, whereas use of a laryngoscope may result in a communication with an emergency medicine department. In other embodiments, the communication management system 130 may determine the closest on-call physician to handle the communication, or it may contact the hospital where the patient is being taken. The communication management system 130 may also connect to multiple remote medical sites.

In some embodiments, the communication management system 130 may directly connect a system in the field with a system used by a consultant or medical professional, it may record transmission of a data stream; store a recording and/or a patient's medical data in a medical record.

In some embodiments, the TFS 132 may also include a billing station for inter-service fees; a quality assurance review module and/or storage of system wide performance data. Optionally the TFS 132 may stream data directly to a known client or broadcast to a network for multiple users.

FIGS. 3A-3D show multiple views of example Telemedicine Base Units according to embodiments of the current invention. An example Telemedicine Base Unit includes a small form factor made of a rugged design, which is preferably IP68 compliant. An example Telemedicine Base Unit includes a camera capable of photographs and video. The example Telemedicine Base Unit is further capable of recording, displaying, and streaming videos taken from a camera on a medical device. The example video and/or audio is optionally stored using a variety of on board, removable or non-removable memory such as a Micro-SD card. The internal memory may be downloaded through removable memory, or may optionally be downloaded through a wired or wireless connection. The device may access a remote data store or access a program that is executed on a remote computer. The video may be streamed with multi-directional audio through a wired or wireless link such as wireless internet, Bluetooth, cellular or satellite communication. Preferably any communication is SIP client compatible because HIPPA encryption is preferable and may be necessary in medical industries. A microphone and speakers may be integrated with the example Telemedicine Base Unit, but may also be connected via wired or wireless connection. A screen on the interface of the device may be a touch screen or may optionally be voice activated/controlled. The screen may be of any size, but preferably would be a 4.3" OLED screen. The example Telemedicine Base Unit may be of modular design and is configured for future expansion for modules such as 3G/4G, satellite, extra battery, GPS, and different expansion buses like USB, OTG, SPI, I2C, CVBS, GPIO, RTC, WDT, HDMI. The example Telemedicine Base Unit may be charged using a wired connection like USB/OTG or by other charging methods such as solar panels. Firmware of the device is optionally upgradable though wired or wireless connection to the device.

Other features of the example Telemedicine Base Unit may include but are not limited to streaming video and multi-directional audio through an integrated wireless network interface. Audio interfacing includes but is not limited to: a speaker, a microphone, Line-in and Line-out, and/or a Bluetooth headset. For future module expandability, the system preferably has an expansion bus, power rails and standard interfaces (like USB, OTG, SPI, I2C, UART, HUART . . . ). The bus may provide interfacing to the external modules like (USB camera, 3G/4G modems, Satellite modems . . . ). An integrated Bluetooth module is able to interface with devices like SPO2, ECG, CO2 and printers with Bluetooth or other wireless capabilities. The example Telemedicine Base Unit is capable of displaying video on LCD and TV (CVBS, HDMI) and also has the capability to overlay text or pictures over a displayed video. For example, graphical symbols made at the remote site, date, time and a logo may be overlaid. All the user adjustable parameters are set through a User Interface such as user interface 114 shown in relation to FIGS. 1 and 2. Recorded audio/video clips preferably include a Date/Time stamp, a location (from an on on-board or connected global positioning system) and a machine name.

The example Telemedicine Base Unit further optionally includes a three phase power management module. It includes a battery that may be charged through USB and/or a direct power supply. The example Telemedicine Base Unit is preferably programmable and can be programmed through a wireless or wired interface. Some of the programmable features include, but are not limited to, time, date, logos; size of recorded video file; Video/Audio stream quality; Wireless interface specifications; Authentication information for remote access and storage; Telemedicine features; Sleep time and wakeup interfaces; Type of events and event alerts; Keypad format and images; and/or Module parameters. As illustratively presented in FIGS. 3a-3d, and set forth above by way of examples, multiple modules having various functionality may be implemented in combination with the TBU 104.

Figure 4A:
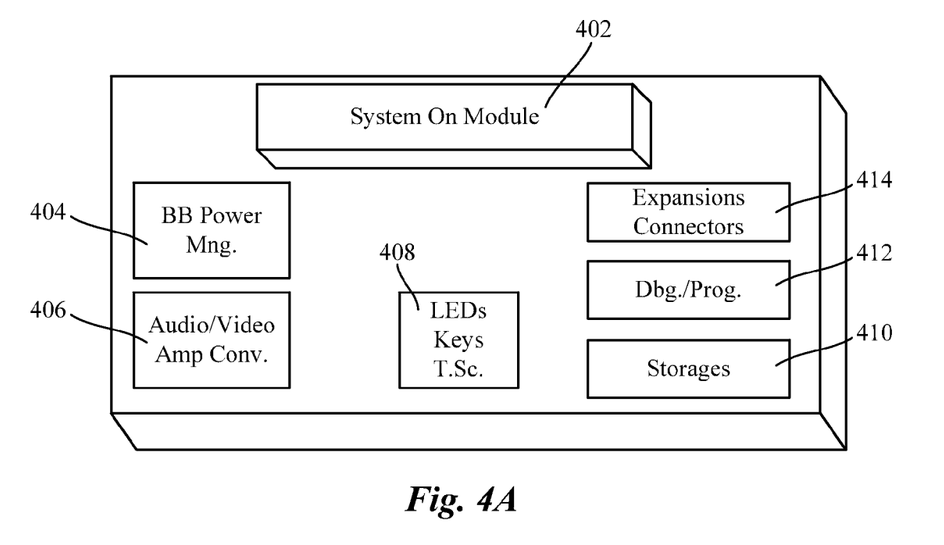
FIGS. 4A and 4B shows a schematic view of a telemedicine base unit according to an embodiment of the current invention.
Figure 4B:
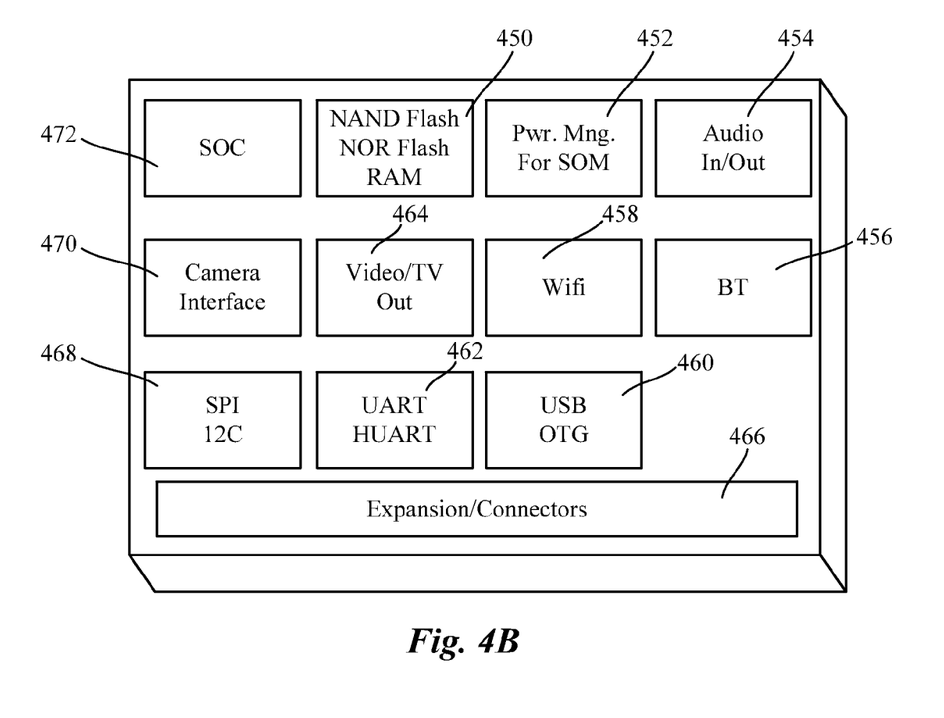

FIGS. 4A and 4B shows a schematic view of a telemedicine base unit according to an embodiment of the current invention. FIG. 4A includes a system on module 402, a power manager 404, audio and video 406, a display 408, storage 410, at least one database and/or at least one program, and expansions and connections 414. FIG. 4B includes Flash RAM 450, power management for system on module 452, audio inputs and outputs 454, Bluetooth 456, wireless 458, USB 460, asynchronous receiver/transmitter 462, video out 464, expansions/connectors 466, microcontroller communication interfaces 468, camera 470, and a system on chip 472.

Figure 5:
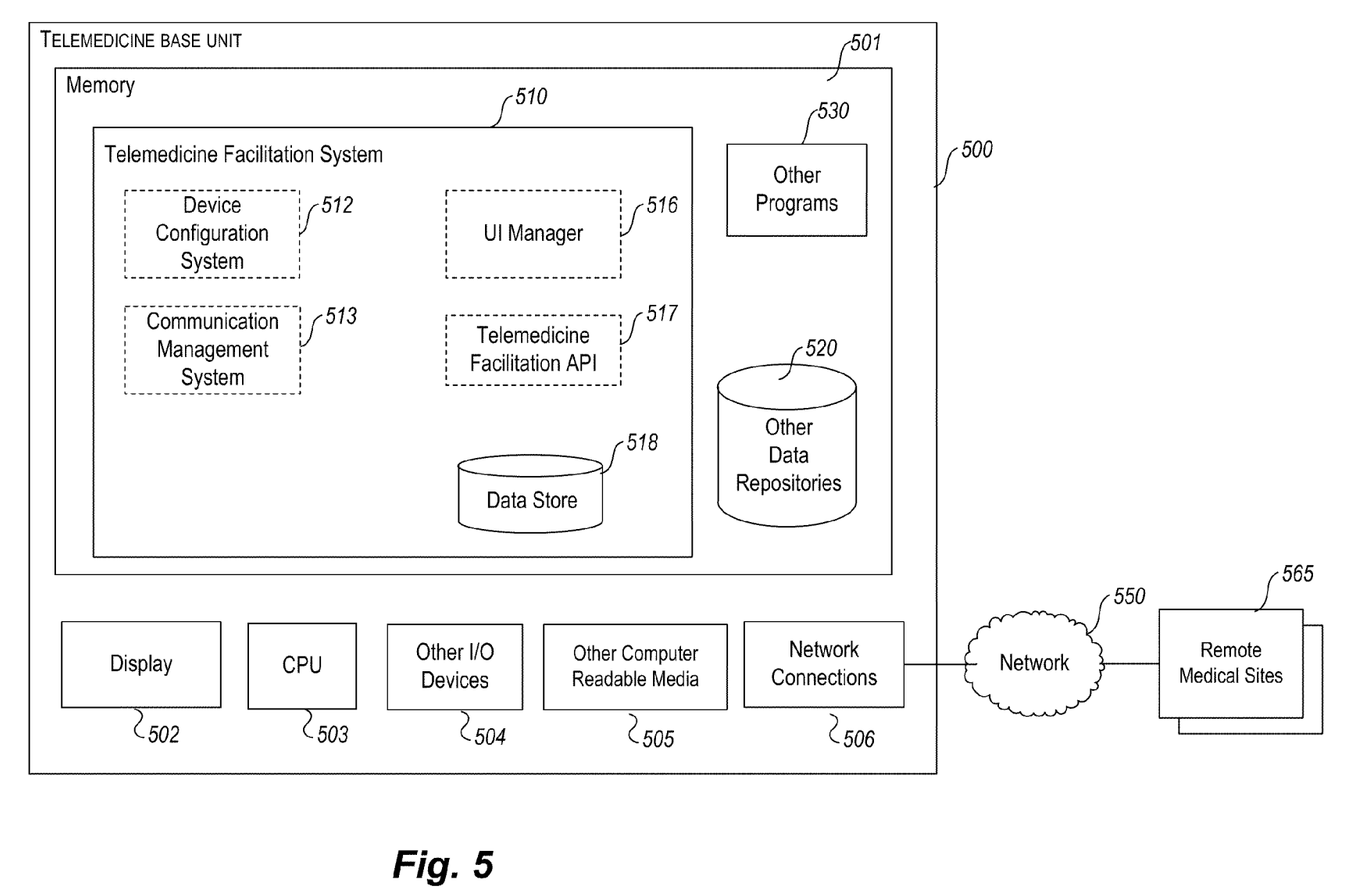
FIG. 5 is an example block diagram of an example Telemedicine Base Unit that enables the execution of a Telemedicine Facilitation System.

FIG. 5 is an example block diagram of an example Telemedicine Base Unit that enables the execution of a Telemedicine Facilitation System. In particular, FIG. 5 shows a Telemedicine Base Unit 500 that may be utilized to implement a Telemedicine Facilitation System 510. Note that one or more general purpose or special purpose computing systems/devices may be used to implement the Telemedicine Facilitation System 510. In addition, the Telemedicine Base Unit 500 may comprise one or more distinct computing systems/devices and may span distributed locations. Furthermore, each block shown may represent one or more such blocks as appropriate to a specific embodiment or may be combined with other blocks. Also, the Telemedicine Facilitation System 510 may be implemented in software, hardware, firmware, or in some combination to achieve the capabilities described herein.

In the embodiment shown, Telemedicine Base Unit 500 comprises a computer memory ("memory") 501, a display 502, one or more Central Processing Units ("CPU") 503, Input/Output devices 504 (e.g., keyboard, mouse, CRT or LCD display, and the like), other computer-readable media 505, and network connections 506. The Telemedicine Facilitation System 510 is shown residing in memory 501. In other embodiments, some portion of the contents, some or all of the components of the Telemedicine Facilitation System 510 may be stored on and/or transmitted over the other computer-readable media 505. The components of the Telemedicine Facilitation System 510 preferably execute on one or more CPUs 503 and execute remote telemedicine operations as described herein. Other code or programs 530 (e.g., an administrative interface, a Web server, and the like) and potentially other data repositories, such as data repository 520, also reside in the memory 501, and preferably execute on one or more CPUs 503. Of note, one or more of the components in FIG. 5 may not be present in any specific implementation. For example, some embodiments may not provide other computer readable media 505 or a display 502.

In a typical embodiment, as described above, the Telemedicine Facilitation System 510 includes a Device Configuration System 512, a Communication Management System 513, a User Interface Manager 516, and a Telemedicine Facilitation API 517. The Telemedicine Facilitation System 510 interacts via a network 550 with remote medical sites 565. The network 550 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX) that facilitate communication between remotely situated humans and/or devices.

In an example embodiment, components/modules of the Telemedicine Facilitation System 510 are implemented using standard programming techniques. For example, the Telemedicine Facilitation System 510 may be implemented as a "native" executable running on the CPU 503, along with one or more static or dynamic libraries. In other embodiments, the Telemedicine Facilitation System 510 may be implemented as instructions processed by a virtual machine that executes as one of the other programs 503. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), and declarative (e.g., SQL, Prolog, and the like).

The embodiments described above may also use either well-known or proprietary synchronous or asynchronous client-server computing techniques. Also, the various components may be implemented using more monolithic programming techniques, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously, and communicate using message passing techniques. Equivalent synchronous embodiments are also supported. Also, other functions could be implemented and/or performed by each component/module, and in different orders, and by different components/modules, yet still achieve the described functions.

In addition, programming interfaces to the data stored as part of the Telemedicine Facilitation System 510, such as in the Telemedicine API 517 can be made available by standard mechanisms such as through C, C++, C#, and Java APIs; libraries for accessing files, databases, or other data repositories; through scripting languages such as XML; or through Web servers, FTP servers, or other types of servers providing access to stored data. The data store 518 may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions described herein.

Furthermore, in some embodiments, some or all of the components of the Telemedicine Facilitation System 510 may be implemented or provided in other manners, such as at least partially in firmware and/or hardware, including, but not limited to one or more application-specific integrated circuits ("ASICs"), standard integrated circuits, controllers executing appropriate instructions, and including microcontrollers and/or embedded controllers, field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network or cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use or provide the contents to perform at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

Figure 6:
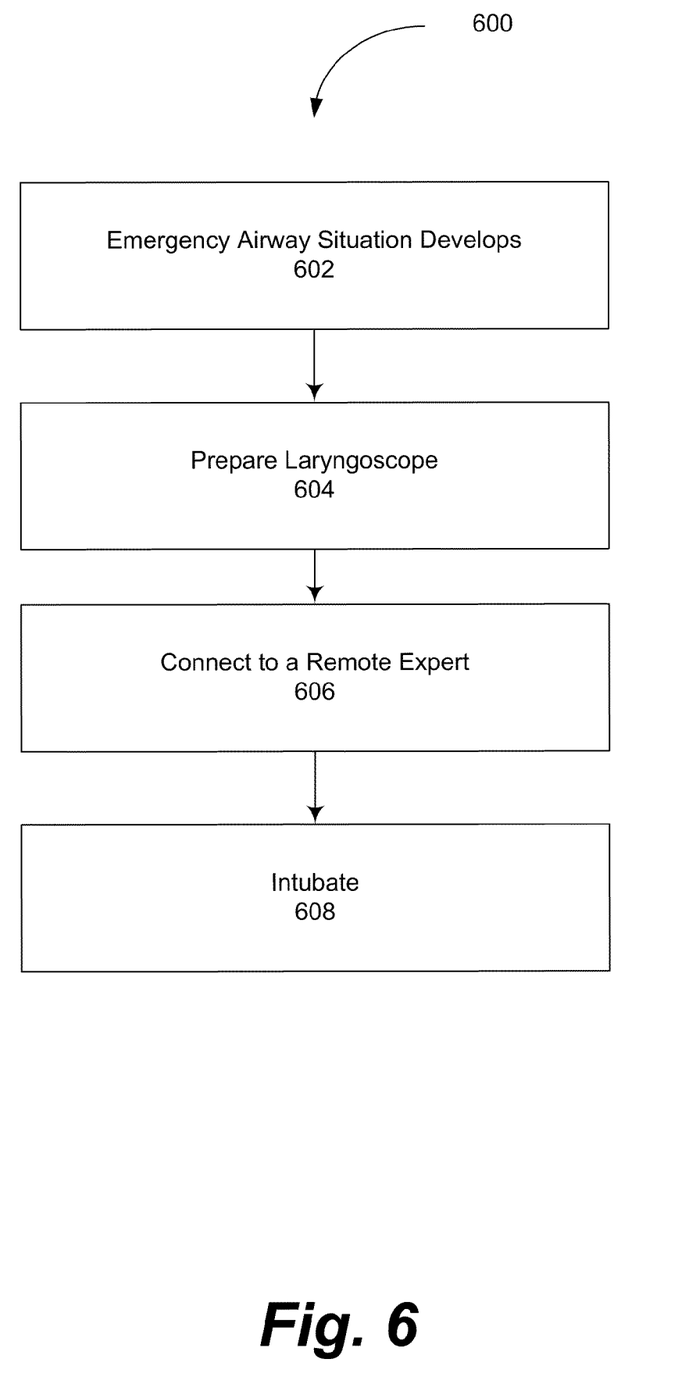
FIG. 6 is a flowchart showing a method 400 for the use of an intubation instrument connected to a telemedicine base unit in an embodiment.

FIG. 6 is a flowchart showing a method 600 for the use of an intubation instrument connected to a telemedicine base unit in an embodiment. By way of example, at block 602 an emergency airway situation develops when an improvised explosive device detonates on a soldier, miles from a hospital. Knowing that an airway is necessary, a medic prepares a laryngoscope for use on the airway at block 604. Preferably the laryngoscope is a video laryngoscope, configured to transmit video signals to a telemedicine base unit that is configured to transmit the video signals over-the-air to an expert in intubation and to receive audio instructions from the expert. The laryngoscope and the telemedicine base unit may be contained in the same housing, and the laryngoscope may already have an endotracheal tube positioned within a channel of the laryngoscope. In an embodiment, the medic may carry a case having a preconfigured laryngoscope with an endotracheal tube within a channel and a telemedicine base unit. At block 606, the medic optionally connects with an on call expert. Using streaming multidirectional video and audio the expert can see and hear the situation and may optionally assist in the intubation procedure. In this case the doctor provides guidance to the medic throughout the intubation as the medic preserves the soldier's airway by intubation at block 608.

Figure 7:
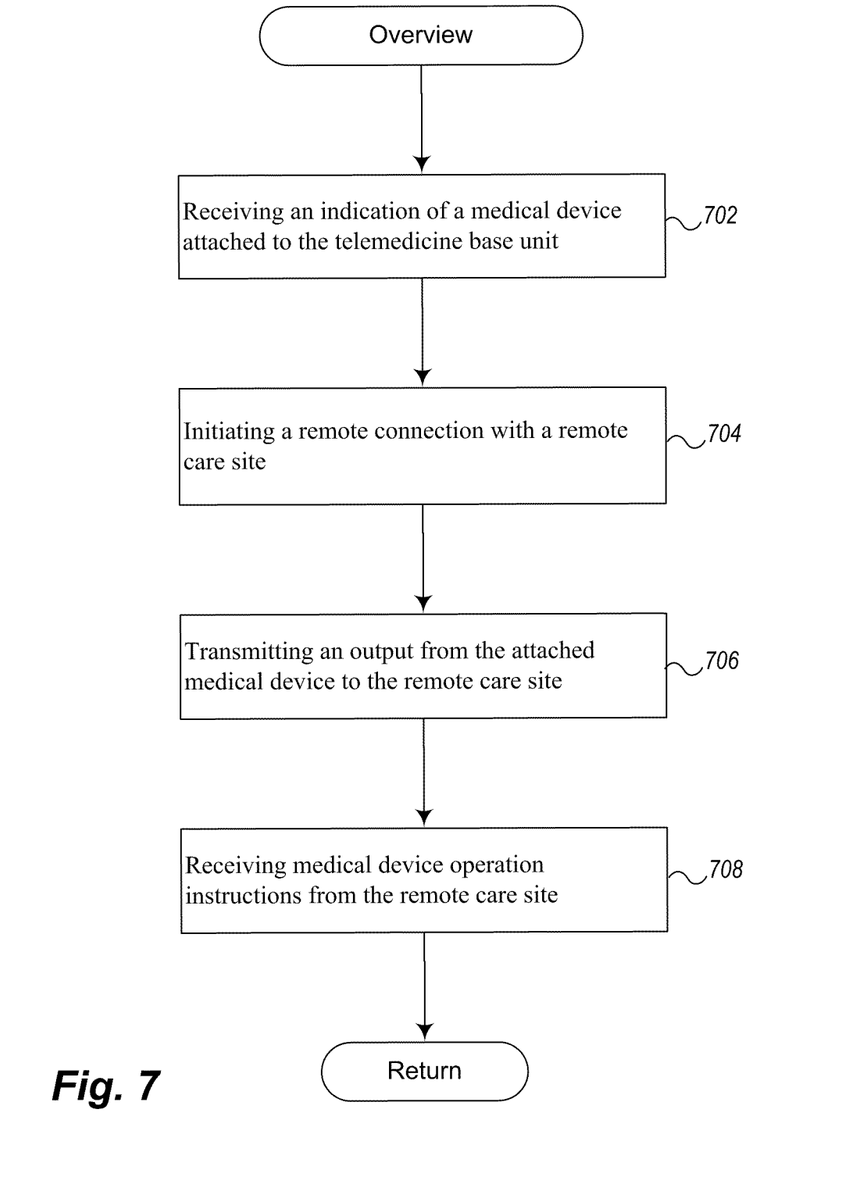
FIG. 7 is an example flow diagram of an overview of an operation of an example Telemedicine Intelligence System.

FIG. 7 is an example flow diagram of an overview of an operation of an example Telemedicine Intelligence System. In particular, FIG. 7 illustrates a process that may be implemented by, for example, one or more elements of the Telemedicine Facilitation System 104 as described with reference to FIG. 1. The illustrated process begins at block 702, where it receives an indication of an attached medical device. The received indication may identify the type or identity of a medical device that was attached to the telemedicine base unit. At block 704, the telemedicine base unit initiates a connection with a remote medical site based on the attached medical device. For example, if the device is a laryngoscope, the device may attempt to initiate contact with an airway specialist or a doctor of emergency medicine. At block 706 the output from the medical device is transmitted to the remote medical care site. The output may include video, patient status, vital signs and/or a heart rate. At block 708, the telemedicine base unit receives medical instructions from the remote medical site. These instructions may include operating instructions or they may be instructions that assist a user in performing a procedure. After block 708 the process performs other processing and/or ends.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A method of operating a telemedicine base unit comprising:
   automatically determining the identity of a medical device attached to a telemedicine base unit;
   automatically selecting, based on the automatic determination of the medical device identity, a remote care site from a plurality of remote care sites based on the determined identity of the attached medical device;
   initiating a remote connection between the base unit and the automatically selected remote care site;
   transmitting to the automatically selected remote care site an output from the medical device attached to the base unit; and
   receiving from the automatically selected remote care site a set of medical device operation instructions chosen, based on the transmitted output from the attached medical device, from a plurality of sets of medical operating instructions.

2. The method of claim 1, further comprising:
   receiving an indication the medical device attached to the telemedicine base unit.

3. The method of claim 1, further comprising:
   transmitting a video and an audio stream from the base unit to the remote care site.

4. The method of claim 3, further comprising:
   receiving patient health data from one or more patient monitoring systems; and
   transmitting the patient health data to the remote care site.

5. The method of claim 4, further comprising:
   receiving the output from the medical device;
   receiving graphical indications form the automatically selected remote care site; and
   overlaying the received graphical indications onto the output from the medical device on a display of the base unit.

6. The method of claim 5, further comprising: receiving a video stream from the automatically selected remote care site; and
   displaying the video stream on the display of the telemedicine device.

7. The method of claim 6, wherein the attached medical device is a laryngoscope with a camera configured to provide an image of an airway, the laryngoscope configured to guide an endotracheal tube.

8. The method of claim 6, wherein the attached device is a disposable electrode vest.

9. A telemedicine device comprising:
   a memory;
   a processor;
   a device configuration system, stored in the memory and configured, when executed on the processor, to determine the identity of an attached medical device of a plurality of medical devices and to configure the telemedicine device to receive output signals from the identified attached medical device; and
   a communication management system, stored in the memory and configured, when executed on the processor, to automatically select, based on the identified medical device, a remote medical site from a plurality of remote medical sites, to provide the selected remote medical site with the output signals from the attached medical device and to receive medical instructions from the selected remote site.

10. The telemedicine device of claim 9, further comprising:
    a housing that encloses internally the memory and the processor;
    a touch screen defined by the housing in communication with the processor and configured to display a user interface display and to receive indications of user touch inputs; and
    a camera in communication with the processor and defined by the housing and configured to provide video of an environment located around the telemedicine device.

11. The telemedicine device of claim 10, further comprising: a health status monitoring system, stored in the memory and configured, when executed on the processor, to receive patient health data from one or more patient monitoring systems.

12. The telemedicine device of claim 11, wherein the memory is configured to store recorded audio and video.

13. The telemedicine device of claim 12, wherein the user interface is further configured to:
    provide an indication of patient health data, wherein the patient health data is at least one of body temperature, pulse rate, blood pressure, blood sugar, and respiratory rate;
    display the output feed from the attached medical device; and
    display graphical indications of a medical instruction received from the remote care site by overlaying the received graphical indications onto an output from the attached medical device on a display of the telemedicine device.

14. The telemedicine device of claim 13, further comprising:
    a video enabled laryngoscope in communication with the telemedicine device, the video enabled laryngoscope configured to provide the telemedicine device with video images of an airway; and
    an endotracheal tube detachably attached in a channel of the video enabled laryngoscope.

15. The telemedicine device of claim 13, further comprising a disposable electrode vest in communication with the telemedicine device.

* * * * *